(12) United States Patent
Dargis et al.

(10) Patent No.: US 10,512,793 B2
(45) Date of Patent: Dec. 24, 2019

(54) RADIATION FLUOROSCOPY APPARATUS

(71) Applicant: SHIMADZU CORPORATION, Nakagyo-Ku, Kyoto-shi, Kyoto (JP)

(72) Inventors: Michel Dargis, Laval (CA); Frederic Hudon, Laval (CA); Wataru Takahashi, Kyoto (JP); Kodai Nagae, Kyoto (JP)

(73) Assignee: SHIMADZU CORPORATION, Kyoto (JP)

( * ) Notice: Subject to any disclaimer, the term of this patent is extended or adjusted under 35 U.S.C. 154(b) by 206 days.

(21) Appl. No.: 15/887,617

(22) Filed: Feb. 2, 2018

(65) Prior Publication Data

US 2019/0240510 A1 Aug. 8, 2019

(51) Int. Cl.
*A61B 6/04* (2006.01)
*A61B 6/12* (2006.01)
(Continued)

(52) U.S. Cl.
CPC .......... *A61N 5/1049* (2013.01); *A61B 6/0492* (2013.01); *A61B 6/08* (2013.01); *A61B 6/12* (2013.01); *A61B 6/4014* (2013.01); *A61B 6/4225* (2013.01); *A61B 6/4266* (2013.01); *A61B 6/4429* (2013.01); *A61B 6/4435* (2013.01); *A61B 6/4452* (2013.01); *A61B 6/487* (2013.01); *A61B 6/542* (2013.01); *A61N 5/1077* (2013.01); *A61B 6/4476* (2013.01); *A61N 2005/1051* (2013.01); *A61N 2005/1061* (2013.01)

(58) Field of Classification Search
CPC ........... A61B 6/0492; A61B 6/08; A61B 6/12; A61B 6/4014; A61B 6/4225; A61B 6/4266; A61B 6/4429; A61B 6/4435; A61B 6/4452; A61B 6/4476; A61B 6/487; A61B 6/542; A61N 5/1049; A61N 5/1077; A61N 2005/1051; A61N 2005/1061
See application file for complete search history.

(56) References Cited

U.S. PATENT DOCUMENTS

2016/0120494 A1 5/2016 Takahashi et al.

FOREIGN PATENT DOCUMENTS

| JP | 2000-167072 | 6/2000 |
|---|---|---|
| JP | 2006-280444 | 10/2006 |

(Continued)

OTHER PUBLICATIONS

JP 2015-156055, Notification of Reasons for Refusal dated Sep. 3, 2018, 3 pages—English, 4 pages—Japanese.

*Primary Examiner* — Mark R Gaworecki
(74) *Attorney, Agent, or Firm* — Andrew F. Young, Esq.; Lackenbach Siegel, LLP

(57) ABSTRACT

A radiation fluoroscopy apparatus detects a marker and includes a control element, an image generation element 61 that generates an image including an embedded marker inside the body of the subject based on a transmitted X-ray. A device candidate detection element 62 detects the candidate of the marker, the local structure detection element 63 detects the local structure in the target region in a proximity of the candidate point of the marker, the device determination element 64 determines whether the local structure is the device such as the marker or not, the device location acquisition element 66 acquires the gravity center coordinate of the local structure, and the device tracking element 67 tracks the marker based on the location of the marker in each frame.

7 Claims, 15 Drawing Sheets

(51) Int. Cl.
*A61B 6/00* (2006.01)
*A61N 5/10* (2006.01)
*A61B 6/08* (2006.01)

(56) References Cited

FOREIGN PATENT DOCUMENTS

JP        2014-128412     7/2014
JP        2014-230606    12/2014

RADIATION FLUOROSCOPY APPARATUS

CROSS REFERENCE TO RELATED APPLICATIONS

This application relates to, but does not claim priority from, JP Ser. No.: 2015-156055 filed Aug. 6, 2015, the entire contents of which are incorporated herein fully by reference.

FIGURE SELECTED FOR PUBLICATION

FIG. 6

BACKGROUND OF THE INVENTION

Field of the Invention

The present invention relates to a radiation fluoroscopy apparatus that detects the position of a marker moving along with a body movement of a subject by taking images including an implanted marker in the body of the subject from two different directions with each other.

Description of the Related Art

A radiation must be irradiated exactly to an affected region relative to the radiation therapy apparatus, having a head that irradiates the therapeutic beam and a gantry that rotates the head around a subject as the center, that performs a radiation therapy by irradiating the therapeutic beam such as e.g., X-ray and an electron beam and so forth to the affected region such as a tumor and so forth. Nevertheless, in some cases, not only the subject unintentionally may move the body thereof, but also the affected area per se may move. For example, a tumor near the lung largely moves depending on breathing. Accordingly, the Patent Document 1 noted below discloses a radiation therapeutic device comprising the system, in which a radiation fluoroscopy apparatus such as an X-ray fluoroscopy device detects the location of a metal marker in place near the tumor and then the therapeutic radiation to be irradiated is controlled thereby.

With regard to such radiation therapy apparatus, the Patent Document 2 noted below discloses an X-ray fluoroscopy apparatus that identifies the location of the marker by fluoroscoping the image including the marker embedded near by the tumor inside the body of the subject. According to Patent Document 2, the X-ray fluoroscopy apparatus detects an implanted marker inside the body by using a first imaging system including a first X-ray tube that irradiates an X-ray from the floor surface side and a first X-ray detector that detects the X-ray that passes through the subject and a second imaging system including a second X-ray tube that irradiates an X-ray from the floor surface side and a second X-ray detector that detects the X-ray that passes through the subject. And 3-dimensional locational data can be acquired by utilizing a 2-dimensional fluoroscopy image imaged by the first imaging system and a 2-dimensional fluoroscopy image imaged by the second imaging system. The marker relative to the affected region along with a movement is detected with a high degree of accuracy by continuously performing such operations and calculating the real-time 3-dimensional locational data of the marker. And an irradiation of the therapeutic radiation is controlled based on the locational data of the marker so that the irradiation of the radiation can be performed with a high degree of accuracy.

RELATED PRIOR ART DOCUMENTS

Patent Document

Patent Document 1: JP Patent Published 2000-167072 A
Patent Document 2: JP Patent Published 2014-128412 A

ASPECTS AND SUMMARY OF THE INVENTION

According to one aspect of the present invention, there is provided a radiation fluoroscopy apparatus having a control element, and an image generation element that generates an image including an embedded marker inside the body of the subject based on a transmitted X-ray. A device candidate detection element detects the candidate of the marker, the local structure detection element detects the local structure in the target region in a proximity of the candidate point of the marker, the device determination element determines whether the local structure is the device such as the marker or not, the device location acquisition element acquires the gravity center coordinate of the local structure, and the device tracking element tracks the marker based on the location of the marker in each frame.

In addition to the sphere marker made of a metal, a non-spherical curved marker that is a metal coil is used as a marker. The projection shape of such curved marker in the image varies due to deformation or rotation while moving, so that the recognition of the marker by using the template matching with a template prepared in advance is not feasible and consequently, the marker may not be tracked.

In addition, when the template matching is applied to detect the marker embedded inside the body, the template of the marker must be prepared. Conventionally, when such template is prepared, an X-ray image, including the marker, of the supine subject on the treatment table is taken and the user extracts the marker portion to obtain the template image, so that tracking of the marker takes a long time. Particularly, in the case of such as, non-coplanar radiation, in which multi direction irradiations from arbitrary angles are performed for the patient by rotating the treatment table, the facing direction of the subject for the X-ray imaging changes one after another and the template must be re-generated in each case. Therefore, the operating time of the radiation therapeutic device for one patient gets longer.

The longer the preparation time until the therapeutic beam is irradiated is, the more the patient whose movement is restricted on the treatment table for such operation feels pain, and consequently, the patient moves during such preparation, so that the irradiation location accuracy of the therapeutic beam can be impaired. In addition, the preparation time should be cut and the throughput of each therapy should be improved so that the therapy opportunity can be provided to more patients.

The purpose of the present invention is to solve the above problem and to provide a radiation fluoroscopy apparatus that can cut the preparation time for the therapy and can detect the marker regardless the shape thereof.

Means for Solving the Problem

According to the first invention, a radiation fluoroscopy apparatus comprises: a radiation source; and a radiation detector that detects the radiation that is irradiated from the radiation source and transmits the subject; wherein the radiation fluoroscopy apparatus detects a device in an image, including the embedded device inside a body of the subject, which is obtained by a fluoroscopy that is carried out from a plurality of directions at a predetermined frame rate, and tracks a movement of the device, and further comprises; an image generation element that generates the image, including the device, based on a detection signal of the radiation detector; a local structure detection element that detects a local structure in the image, including the device, that the image generation element generates; a device determination element that determines whether the local structure detected by the local structure detection element is the device or not; a device location acquisition element that acquires the location of the local structure in the image as the location of the device that is determined by the device determination element as the device; and a device tracking element that tracks the device based on the location of the device in each frame obtained by the device location determination element.

According to the second invention, an X-ray fluoroscopy apparatus further comprises: a device candidate detection element that detects a candidate of the device in the image including the device, wherein the local structure detection element detects the local structure in the proximity of the candidate of the device that is detected by the device candidate detection element.

According to the third invention, an X-ray fluoroscopy apparatus further comprises: a local structure expanding element that detects one overall structure corresponding to the entire device based on the local structure when the device determination element determines that the local structure is the device and further determines that the local structure is a part of the device.

According to an aspect of the fourth invention, the device location acquisition element that acquires a gravity center of the local structure as the location of the local structure that the device determination element determines as the device.

According to an aspect of the fifth invention, the device location acquisition element that acquires a gravity center, an end point and a center point of the overall structure, which is acquired by the local structure expanding element, as the location of the device, which the device location acquisition element acquires.

Effect of the Invention

According to the first to the fifth inventions, the local structure detection element that detects the local structure including the device, the device determination element whether the local structure is the device or not, the device location acquisition element that acquires the location of the local structure in the image as the location of the device, and the device tracking element that tracks the device based on the location of the device in each frame are installed, so that the fluoroscopy that generates a template is not required as the device tracking relative to the conventional the template matching. Therefore, the constrained time against the patient on the treatment table for the radiation therapy apparatus can be cut in addition, it is determined whether the local structure is the device or not, so that not only a plurality of templates for the curved marker having a variety of directions, lengths and shapes depending on the fluoroscopy direction and the embedded place are not generated, no repeat template matching operation in the conventional template matching relative to the plurality of templates is required, and the throughput of the radiation therapy apparatus can be improved, but also the tracking of the device, such as a marker, that changes the shape per se in the image can be accurately executed, According to an aspect of the second invention, the device candidate detection element detects the device candidate in the image in which the static structures such as hone and so forth incorporated in the same image as the image of the device is eliminated by fluoroscopy, so that the errant detection of the device due to the effect of the bone and a noise can be minimized.

According to the third invention, the local structure expanding element can get accurately the overall image of the curved marker that provides a variety of directions, lengths and shapes depending on the fluoroscopy direction and the embedded place.

According to an aspect of the fourth invention, the device location acquisition element acquires the gravity center of the local structure as the location of the device, so that the accurate tracking for the device in the unit of a sub-pixel can be executed.

According to an aspect of the fifth invention, the device location acquisition element acquires the gravity center, the end point, the center point of the overall structure as the location of the device, so that the accurate tracking for the device in the unit of a sub-pixel can be executed despite the marker providing the variety of directions, lengths and shapes depending on the fluoroscopy direction and the embedded place.

The above and other aspects, features and advantages of the present invention will become apparent from the following description read in conjunction with the accompanying drawings, in which like reference numerals designate the same elements.

DETAILED DESCRIPTION OF THE PREFERRED EMBODIMENTS

Figure 1:
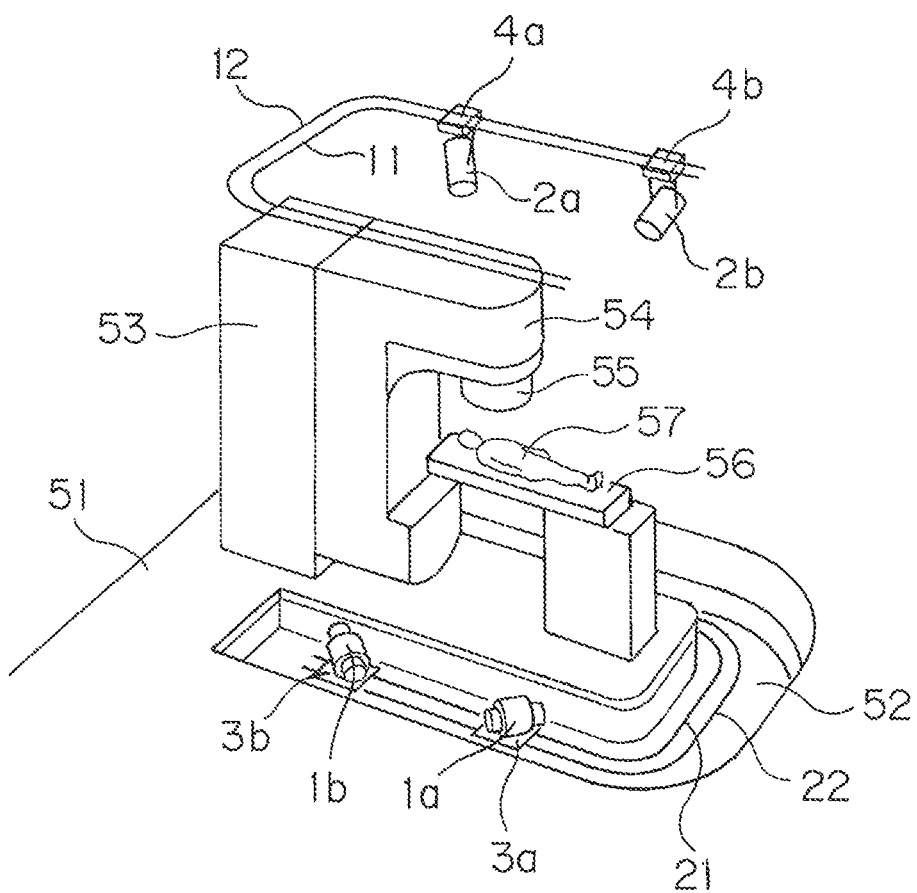
FIG. 1 is a perspective view of the radiation fluoroscopy apparatus applying the X-ray fluoroscopy device of the present invention.

Reference will now be made in detail to embodiments of the invention. Wherever possible, same or similar reference numerals are used in the drawings and the description to refer to the same or like parts or steps. The drawings are in simplified form and are not to precise scale. The word 'couple' and similar terms do not necessarily denote direct and immediate connections, but also include connections through intermediate elements or devices. For purposes of convenience and clarity only, directional (up/down, etc.) or motional (forward/back, etc.) terms may be used with respect to the drawings. These and similar directional terms should not be construed to limit the scope in any manner. It will also be understood that other embodiments may be utilized without departing from the scope of the present invention, and that the detailed description is not to be taken in a limiting sense, and that elements may be differently positioned, or otherwise noted as in the appended claims without requirements of the written description being required thereto.

Various operations may be described as multiple discrete operations in turn, in a manner that may be helpful in understanding embodiments of the present invention; however, the order of description should not be construed to imply that these operations are order dependent.

If used herein, a computer related or based system includes an input device for receiving data in any form, an output device for outputting data in any tangible form (e.g. transmitting, printing, transmitting, relaying, calculating, or displaying on a computer screen, etc.), a memory for storing data as well as computer code, and a microprocessor for executing computer code wherein said computer code resident in said permanent memory will physically cause said microprocessor to read-in data via said input device, process said data within said microprocessor and output said processed data via said output device.

It will be further understood by those of skill in the art that the apparatus and devices and the elements herein, without limitation, and including the sub components such as operational structures, circuits, communication pathways, and related elements, control elements of all kinds, display circuits and display systems and elements, any necessary driving elements, inputs, sensors, detectors, memory elements, processors and any combinations of these structures etc. as will be understood by those of skill in the art as also being identified as or capable of operating the movement, guidance, control and operational systems and devices and subcomponents noted herein and structures that accomplish the functions without restrictive language or label requirements since those of skill in the art are well versed in related diagnostic devices, computer and operational controls and technologies of radiographic devices and all their sub components, including various circuits and combinations of circuits without departing from the scope and spirit of the present invention.

Figure 2:
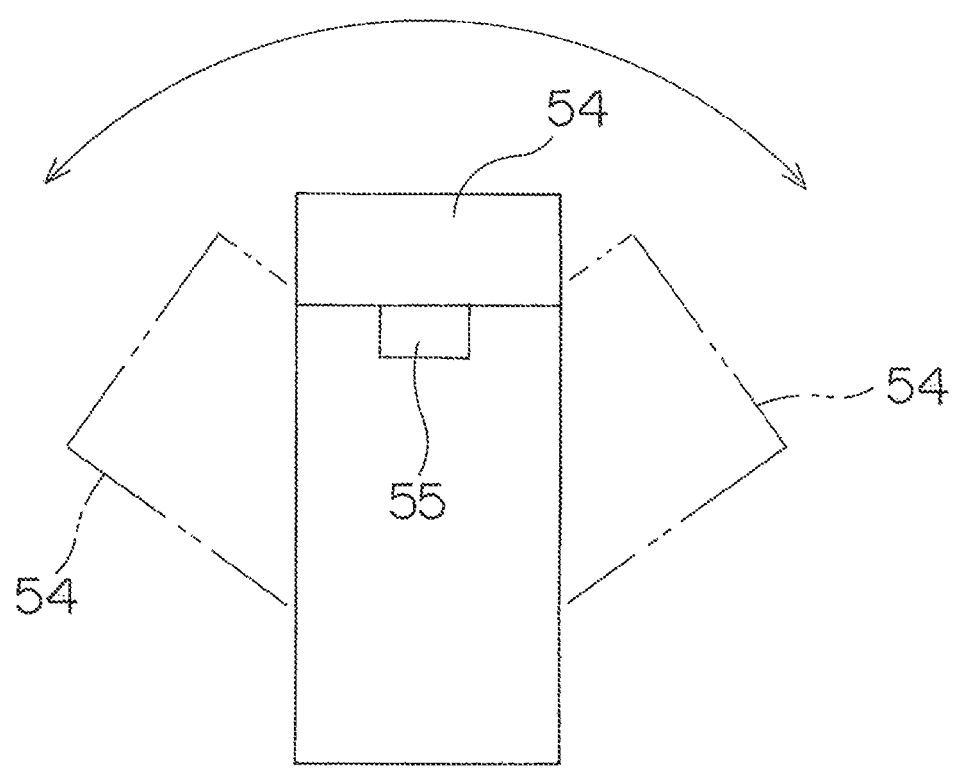
FIG. 2 is an explanatory drawing of the oscillating operation of the head 55 and the head support 54 relative to the radiation therapy apparatus.

The inventor sets forth Embodiments of the present invention based on the following FIG. 1 is a perspective view of the radiation therapy apparatus applying the X-ray fluoroscopy device of the present invention. FIG. 2 is an explanatory drawing of the oscillating operation of the head 55 and the head support 54 relative to the radiation therapy apparatus.

The present radiation therapy apparatus that is to provide a radiation therapy by irradiating an X-ray or an electron beam to the affected area of the subject 57 lying on the table 56 comprises a gantry 53 installed on the floor 51 of the treatment room, a head support element 54 that oscillates around the axis facing the horizontal direction relative to the gantry 53 and a head 55 supported by the head support element 54 to irradiate the radiation to the subject 57. The head 55 can irradiate the radiation to the affected area of the subject 57 from a variety of angles with the oscillating operation of the head support element 54.

On performing a radiation therapy, the radiation must be accurately irradiated to the affected area. For such purpose, a marker is in-place near the affected area. The marker embedded inside the body is continuously looked at through the first X-ray fluoroscopy mechanism and the second X-ray fluoroscopy mechanism and the 3-dimensional locational information relative to the marker is calculated from the 2-dimensional fluoroscopy images obtained by the first X-ray fluoroscopy mechanism and the second X-ray fluoroscopy mechanism so that the marker can be detected with a high degree of accuracy.

For the purpose of execution of such fluoroscopy, the radiation fluoroscopy apparatus according to the aspect of the present invention, which is applied to the radiation therapy apparatus, is an X-ray fluoroscopy apparatus comprising an X-ray tube as a radiation source and an X-ray detector as a radiation detector. The X-ray fluoroscopy device in order to perform such fluoroscopy operation comprises the first X-ray fluoroscopy mechanism consisting of the first X-ray tube 1a and the first X-ray detector 2a and the second X-ray fluoroscopy mechanism consisting of the second X-ray tube 1b and the second X-ray detector 2b, and further comprises the moving mechanism that moves the first X-ray tube 1a and the first X-ray detector 2a to the first fluoroscopy location and the second fluoroscopy location, as described later, to be in-place facing each other and also the second X-ray tube 1b and the second X-ray detector 2b to the first fluoroscopy location and the second fluoroscopy location to be in-place facing each other. Further, an image intensifier (I.I) or a flat panel detector (FPD) is used as the first X-ray detector 2a and the second X-ray detector 2b.

The first X-ray tube 1a is supported with the first pedestal 3a for the X-ray tube. Further, the second X-ray tube 1b is supported with the second pedestal 3b for the X-ray tube. The first rail 21 for the X-ray tube having approximately U-shape, in which two linear portions are connected with the connection element including circular portion, and the second rail 22 for the X-ray tube having approximately U-shape as the same as the first rail 21 for the X-ray tube, in which two linear portions are connected through the connection element including a circular portion, are installed on the bottom surface 52 of the concave portion formed on the floor 51 in the imaging room. The first rail 21 and the second rail 22 for the X-ray tube for such X-ray tubes are in-place in parallel with each other. And the first pedestal 3a for the X-ray tube and the second pedestal 3b for the X-ray tube move to the first fluoroscopy position and the second fluoroscopy position, as described later, by guiding with the first rail 21 and the second rail 22.

The first X-ray detector 2a is supported with the first pedestal 4a for the X-ray detector. Further, the second X-ray detector 2b is supported with the second pedestal 4b for the X-ray detector. The first rail 11 for the X-ray detector having approximately U-shape, in which two linear portions are connected through the connection element including a circular portion, and the second rail 12 for the X-ray tube having approximately U-shape as the same as the first rail 11 for the X-ray tube, in which two linear portions are connected through the connection element including a circular portion, are suspended from the ceiling of the imaging room. The first rail 11 for the X-ray detector and the second rail 12 for the X-ray detector are in-place in parallel with each other. And the first pedestal 4a for the X-ray detector and the second pedestal 4b for the X-ray detector move to the first fluoroscopy position and the second fluoroscopy position, as described later, by guiding with the first rail 11 and the second rail 12.

In addition, even though it is not drawn in FIG. 1, the concave areas formed on the floor 51 are covered with a covering member forming a part of the floor, so that the first X-ray detector 2a and the second X-ray detector 2b are in-place under the floor.

Figure 3:
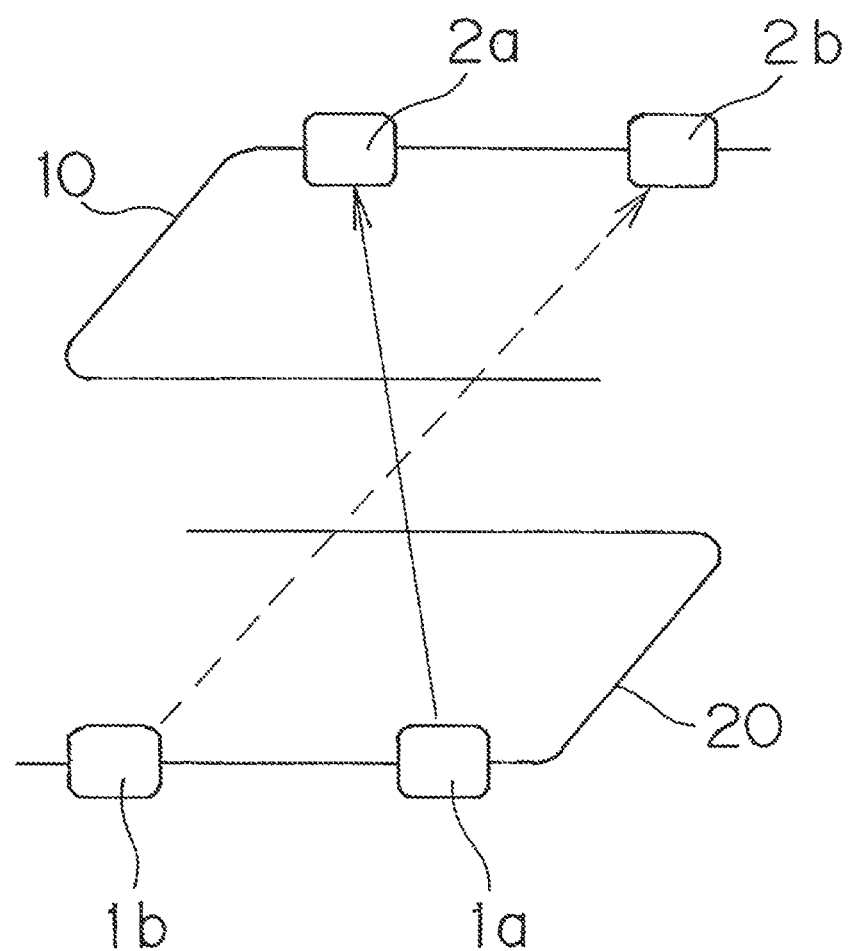
FIG. 3 is an explanatory drawing of the in-place state, in which the first X-ray tube 1a, the second X-ray tube 1b, the first X-ray detector 2a and the second x-ray detector 2b are respectively in-place in the first fluoroscopy position.

FIG. 3, 4, 5 are explanatory drawings of the state in-place, in which each of the first X-ray tube 1a, the second X-ray tube 1b, the first X-ray detector 2a and the second X-ray detector 2b is in-place in the first fluoroscopy position and the second fluoroscopy position.

Figure 4:
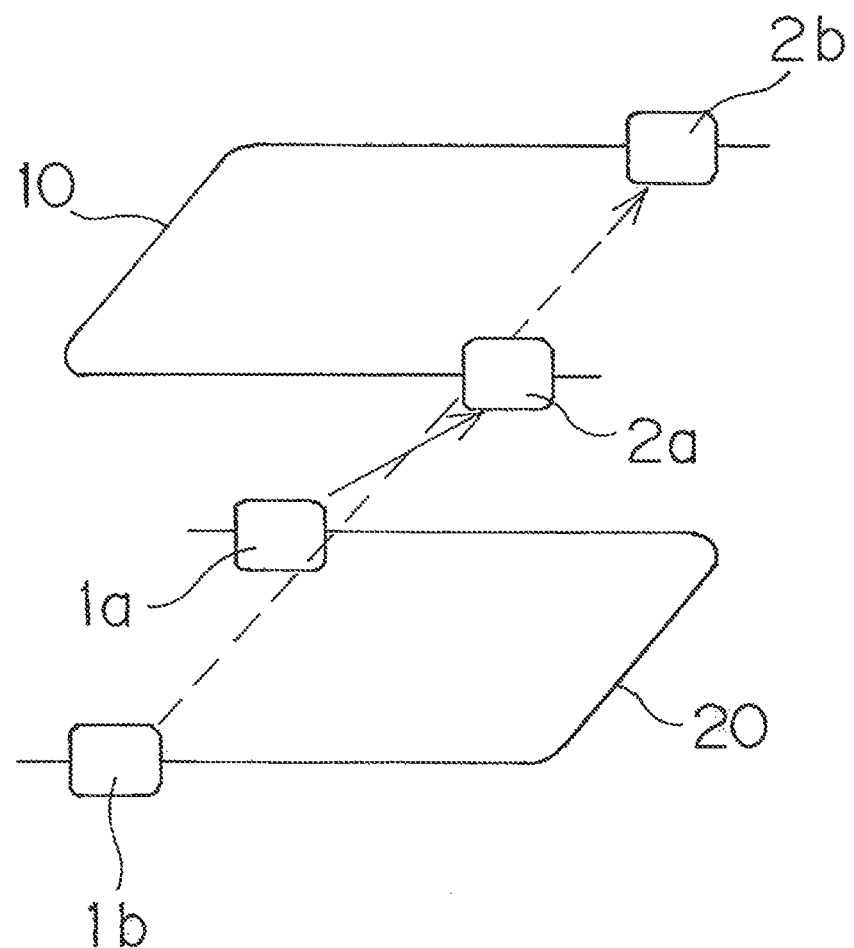
FIG. 4 is an explanatory drawing of the in-place state, in which each the first X-ray tube 1a, the second X-ray tube 1b, the first X-ray detector 2a and the second x-ray detector 2b are arranged in the first fluoroscopy position and the second fluoroscopy position.
Figure 5:
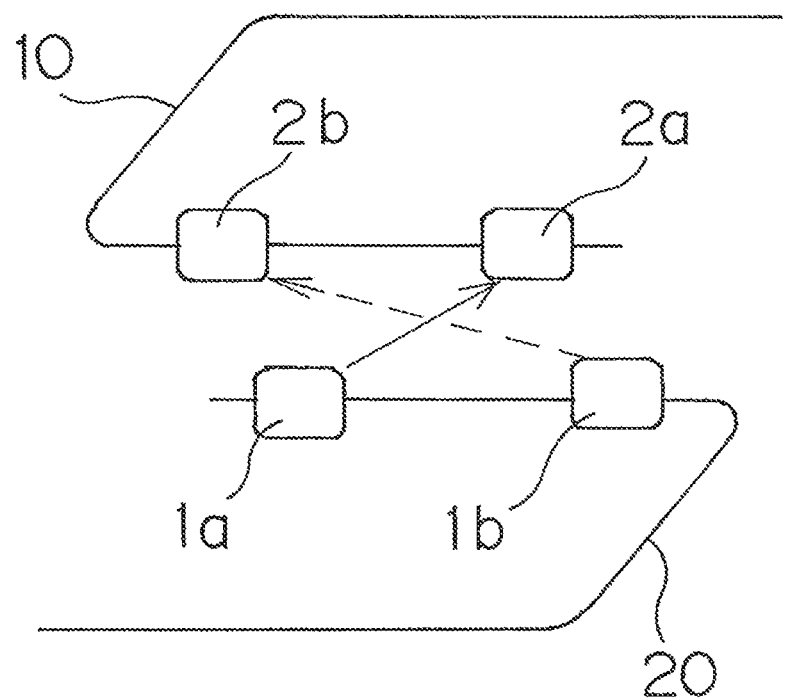
FIG. 5 is an explanatory drawing of the in-place state, in which the first X-ray tube 1a, the second X-ray tube 1b, the first X-ray detector a and the second x-ray detector 2b are respectively arranged in the second fluoroscopy position.

The X-ray fluoroscopy apparatus fluoroscopes the subject 57 from two different directions to each other at three preset positions. FIG. 3 is the state, in which the first X-ray tube 1a, the second X-ray tube 1b, the first X-ray detector 2a and the second x-ray detector 2b fluoroscope the subject 57 from two different directions to each other at the first position, FIG. 4 is the state, in which the first X-ray tube 1a, the second X-ray tube 1b, the first X-ray detector 2a and the second x-ray detector 2b fluoroscope the subject 57 from two different directions to each other at the second position, and FIG. 5 is the state, in which the first X-ray tube 1a, the second X-ray tube 1b, the first X-ray detector 2a and the second x-ray detector 2b fluoroscope the subject 57 from two different directions to each other at the third position.

Accordingly, the X-ray fluoroscopy apparatus fluoroscopes the subject 57 from two different directions to each other at the three positions so that, referring to FIG. 2, the head 55 can execute the X-ray fluoroscopy without interfering the fluoroscopy field even when the head 55 of the radiation therapy apparatus irradiates the radiation to the subject 57 from a variety of angles. And at such three positions, the first X-ray tube 1a, the second X-ray tube 1b and the first X-ray detector 2a and the second X-ray detector 2b are in-place in either one of the preset first fluoroscopy position or the preset second fluoroscopy position.

Specifically, referring to FIG. 3, in the first position, the first X-ray tube 1a is in-place in the first fluoroscopy position, the second X-ray tube 1b is in-place in the first fluoroscopy position, the first X-ray detector 2a is in-place in the first fluoroscopy position, and the second X-ray detector 2b is in-place in the first fluoroscopy position, respectively. Referring to FIG. 4, in the second position, the first X-ray tube 1a is in-place in the second fluoroscopy position, the second X-ray tube 1b is in-place in the first fluoroscopy position, the first X-ray detector 2a is in-place in the second fluoroscopy position, and the second X-ray detector 2b is in-place in the first fluoroscopy position, respectively. Referring to FIG. 5, in the third position, the first X-ray tube 1a is in-place in the second fluoroscopy position, the second X-ray tube 1b is in-place in the second fluoroscopy position, the first X-ray detector 2a is in-place in the second fluoroscopy position, and the second X-ray detector 2b is in-place in the second fluoroscopy position, respectively.

The first pedestal 3a for the X-ray tube and the second pedestal 3b for the X-ray tube move along the move passage 20 consisting of the first rail 21 and the second rail 22 so that the first X-ray tube 1a and the second X-ray tube 1b can be in-place in the first fluoroscopy position and the second fluoroscopy position, respectively. Further, the first pedestal 4a for the X-ray detector and the second pedestal 4b for the X-ray detector move along the move passage 10 consisting of the first rail 11 and the second rail 12 so that the first X-ray detector 2a and the second X-ray detector 2b can be in-place in the first fluoroscopy position and the second fluoroscopy position, respectively.

In addition, according to the aspect of the Embodiment, both the first rail 11 for the X-ray detector and the second rail 12 for the X-ray detector, and both the first rail 21 for the X-ray tube and the second rail 22 for the X-ray tub have an approximately U-like shape in which two linear members are connected through a connection member including circular members. Therefore, the first X-ray tube 1a, the second X-ray tube 1b, the first X-ray detector 2a and the second X-ray detector 2b move in the horizontal direction from the first position in FIG. 3, the second position in FIG. 4 and the third position in FIG. 5 in synchronism with each other, so that the X-ray fluoroscopy position can be moved in the horizontal direction. Therefore, fix example, even when the marker and so forth is out of the fluoroscopy range during the X-ray fluoroscopy, the first X-ray tube 1a, the second X-ray tube 1b, the first X-ray detector 2a and the second X-ray detector 2b move in the horizontal direction in synchronism with each other, so that the marker and so forth can be tracked.

Figure 6:
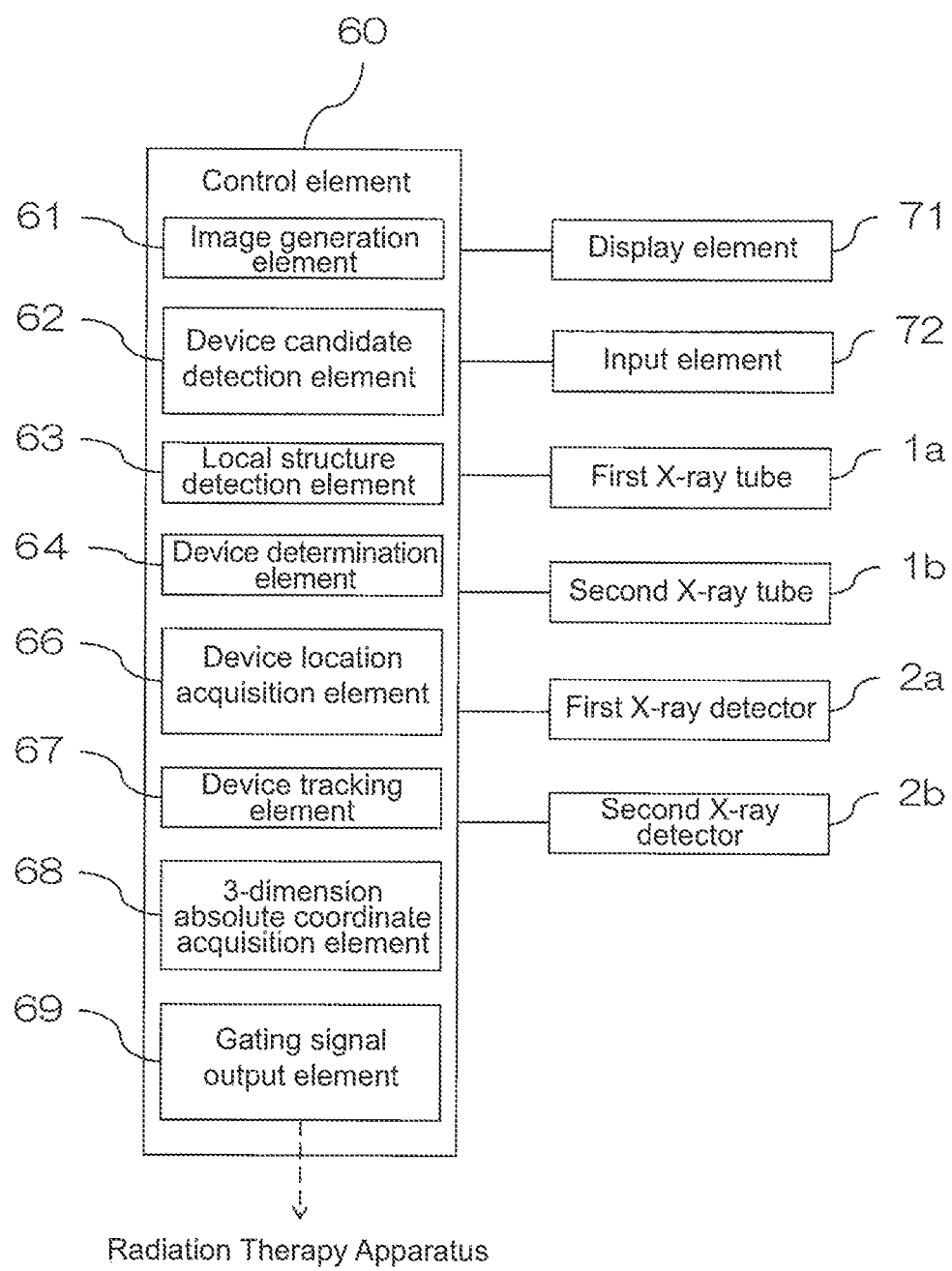
FIG. 6 is a block diagram illustrating the main control system of the X-ray fluoroscopy apparatus according to an aspect of the Embodiment 1 of the present invention.

FIG. 6 is a block diagram illustrating the main control system of the X-ray fluoroscopy apparatus according to the aspect of the present invention.

Such X-ray fluoroscopy apparatus comprises a CPU that executes the logic operation, a ROM that stores operation programs required to control the apparatus, a RAM that stores temporally the data and so forth when controlling, and so forth and further comprises a control element 60 that controls the entire apparatus. The control element 60 is connected, as described above, to the first X-ray tube 1a, the second X-ray tube 1b, the first X-ray detector 2a and the second X-ray detector 2b. In addition, the control element 60 is connected to a display element 71 that displays the image and so forth relative to the subject 57, an input element 72 such as a mouse and a keyboard that the operator inputs a variety of settings, and to the X-ray therapy apparatus in FIG. 1.

The control element 60 comprises, as functional elements, an image generation element 61 that generates an image including the marker embedded inside the body of the subject 57 based on the transmitted X-rays that the first X-ray detector 2a and the second X-ray detector 2b detect, the device candidate detection element 62 that detects the marker candidate, the local structure detection element 63 that detects the local structure in the target region in the proximity of the marker candidate, the device determination element 64 that determines whether the local structure is the device such as the marker and so forth or not, the device location acquisition element 66 that seeks the gravity coordinate of the local structure, the device tracking element 67 that tracks the marker based on the location of the device in each frame, a 3-dimension absolute coordinate acquisition element 68 that acquires a 3-dimension absolute coordinate of the marker from the tracking result of the position of each marker and so forth, and a gating signal output element 69 that sends the gating signal to the radiation therapy apparatus based on the 3-dimension absolute coordinate of the marker.

Figure 7A:
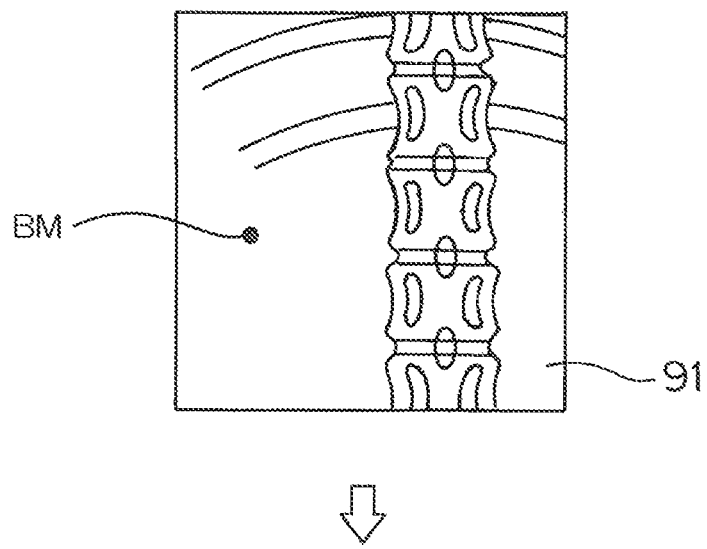
FIG. 7A, 7B are schematic views illustrating the operation of the device candidate detection element 62.
Figure 7B:
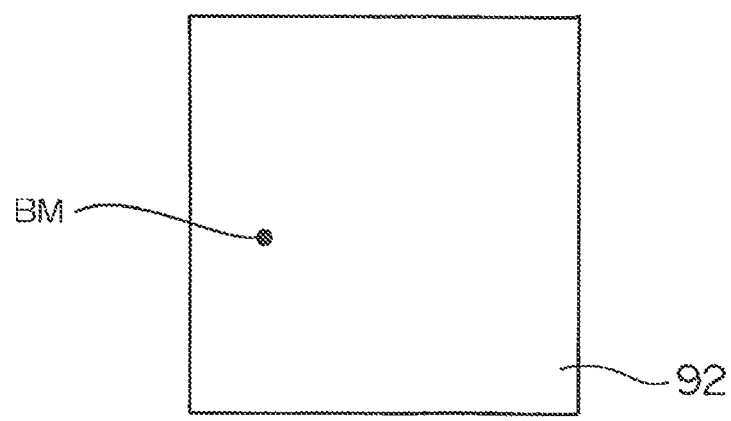
Figure 8:
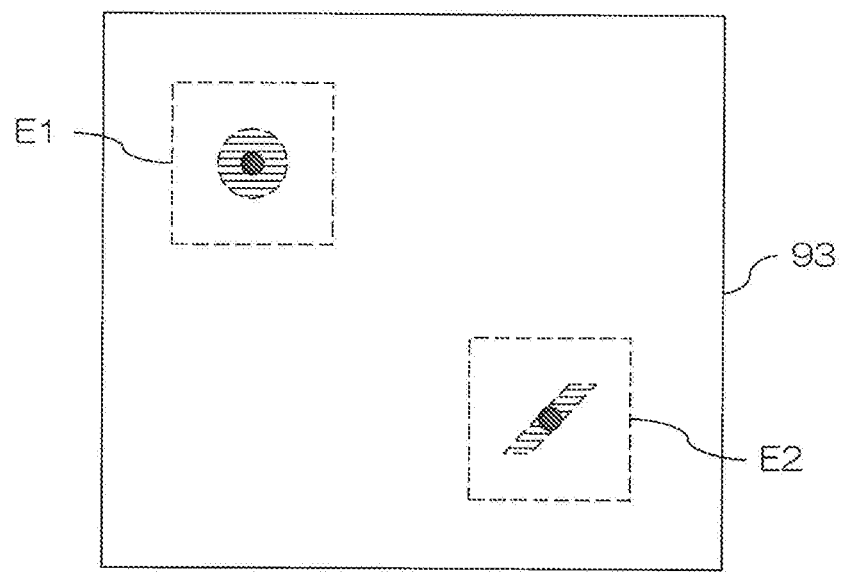
FIG. 8 is a schematic view illustrating the operation of the local structure detection element 63.
Figure 9:
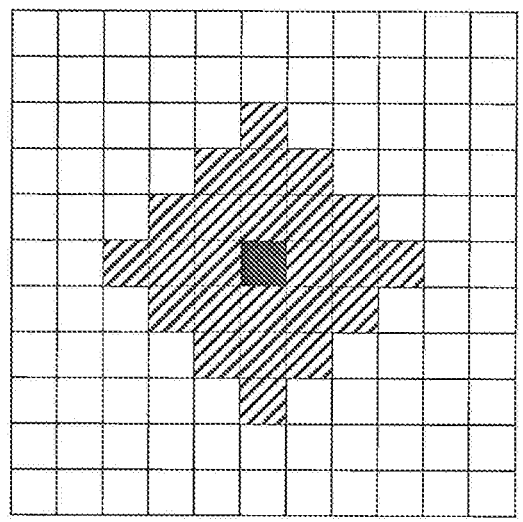
FIG. 9 is a schematic view illustrating the operation of the local structure detection element 63.
Figure 10:
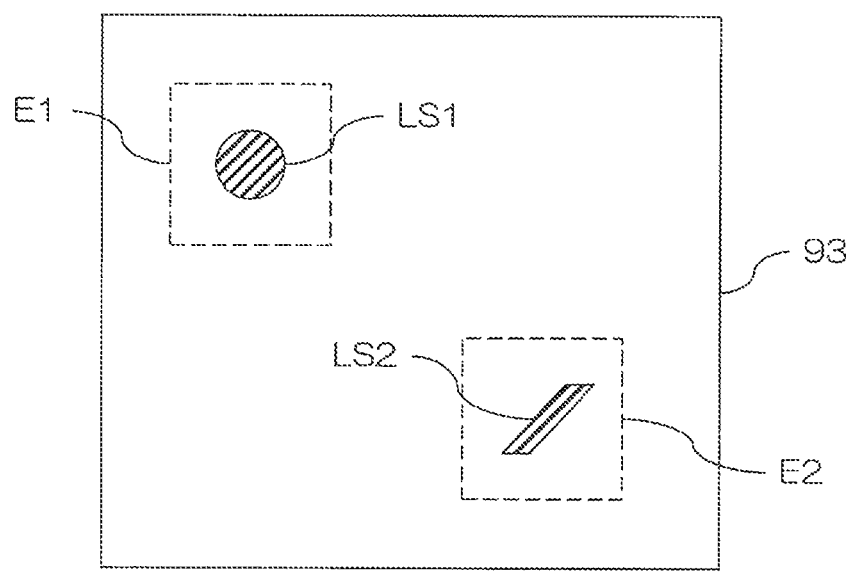
FIG. 10 is a schematic view illustrating the operation of the device determination element 64.
Figure 11:
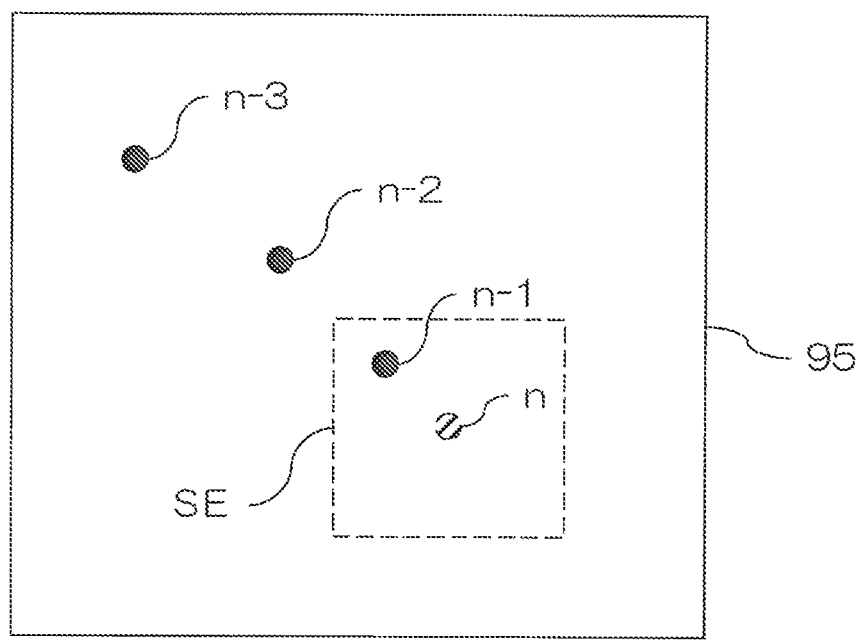
FIG. 11 is a schematic view illustrating the operation of the device tracking element 67.

Next, the inventor sets forth the operation of each functional aspect of the control element 60 on the basis of an example of the case in which the marker embedded in the body of the subject 57 is the spherical marker. FIG. 7A, 7B are schematic views illustrating the operation of the device candidate detection element 62. FIG. 8 and FIG. 9 are schematic views illustrating the operation of the local structure detection element 63. FIG. 10 is a schematic view illustrating the operation of the device determination element 64. FIG. 11 is a schematic view illustrating the operation of the device tracking element 67.

First, the two selected imaging, systems acquire images, including the marker embedded inside the body of the subject 57, from the two directions at the frame rate approximately in the range of 20 to 30 fps. Specifically, the image generation element 61 generates the X-ray images at the constant frame rate based on the electric signals from the first X-ray detector 2a and the second X-ray detector 2b that are in-place in the predetermined fluoroscopy position according to the selection of the imaging system.

The device candidate detection element 62 detects the candidate point of the spherical marker BM from the image that the image generation element 61. Referring to FIG. 7A, the image 91 includes a structural element other than the spherical marker Bivi and noises and the static structural element such as bone and so forth taken in the image 91 with a high contrast may lower the detection efficiency of the marker. Therefore, referring to FIG. 7B, the device candidate detection element 62 detects the candidate of the spherical marker BM from the image 92 that is the image of the image 91 from which the static structural element such as bone is removed. The spherical marker BM that strongly absorbs X-ray is recognized as a dark point moving between a plurality of continuous images, so that the static structural element other than the spherical marker BM can be removed from the image by subtracting the averaged image of images corresponding to the previous few frames from the image corresponding to the frame at the certain timing. Therefore, the chance at which a noise and so forth other than the spherical marker BM is erroneously detected as the candidate point of the marker can be minimized, so that an efficiency of the marker recognition can be improved.

In addition, e.g., a known method using a Laplacian filter relative to the image of which the static structural element is removed can be applied to detection of the candidate point of the spherical marker BM using the device candidate detection element 62. The method of such as reducing the image size corresponding to the size of the spherical marker BM can be applied to speed up the processing. In addition, the operator can specify manually the candidate point of the device through the input element 72 without installing the device candidate detection element 62.

Referring to FIG. 8, the local structure detection element 63 executes the local segmentation (region segmentation) in a proximity of the candidate point of the spherical marker BM that the device candidate detection element 62 detects in the target regions E1, E2, and detects the local structure. In addition, referring to FIG. 8, the black circle is the candidate point of the spherical marker BM. The local structure detection element 63 executes the processing (segmentation) to extract the pattern having a regularity in such target regions E1, E2 using the pixel values of the candidate point and the proximity thereof. In addition, the size of the spherical marker BM incorporated in the image 93 is known in advance, so that the predetermined target regions E1, E2 are specified by placing a rectangular frame that has the length on a side, which is e.g., approximately 2-3 times larger than the diameter of the spherical marker BM having a circular shape in the image 93, in the image 93 that centers on the candidate point.

In addition, the spherical marker BM overlaps a variety of structure elements inside the body depending the embedded location, so that the background of the spherical marker BM incorporated in the image is not with uniformity and in addition, the pixel value of each spherical marker BM takes a variety of values. Accordingly, when executing the local segmentation in a proximity of the spherical marker BM, the parameters are changed and specified arbitrarily every candidate point. For example, referring to FIG. 9, a value of the constant area on the basis of the pixel value at the candidate point (indicated by the black square in FIG. 9) is specified every candidate point and an operation by which the same label (indicated by the hatching in FIG. 9) is given to the pixel, which meets the condition relative to the set-up pixel value, in the proximity of the candidate point is executed, so that a bundle of regions, in which the pixels having the same label are continuously present, is extracted as a local structure. In addition, referring to FIG. 9, one square corresponds to one pixel.

In addition, the detection of the local structure in the limited region centering on the candidate point of the spherical marker BM in the image 93 using the local structure detection element 63 can be achieved using the other known method than the above segmentation utilizing the pixel value. For example, the local structure can be extracted by detecting an outline of the local structure in the proximity of the candidate point of the spherical marker. BM utilizing a variation of brightness of the digital image due to the edge detection by the Canny method, and the local structure can be extracted by binarization using the discriminant analysis method. In addition, instead of the image 93 that is used to detect the local structure by the local structure detection element 63, both the image 91 that the operation of the image generation element 61 acquire and the image 92 in which the device candidate detection element 62 is operative to remove the static structural element such bone and so forth can be applied thereto.

The device determination element 64 determines whether the local structure that the local structure detection element 63 detects is the device such as a marker and so forth or not. The spherical marker BM that is a sphere appears always in a circular form in the image and in addition, the size thereof is known in advance. Therefore, the local structure that have the shape in a circular form and the area that is in the predetermined range of size is determined as the spherical marker BM. The determination whether the local structure is in the circular form or not can be executed, for example, by utilizing that the responses to the Gabor filter of 8 directions are equal in all directions. In addition, the local structure is determined whether the spherical marker or not by calculating the degree of circularity that is a benchmark indicating how close the target shape is to the circular form. In such way, referring to FIG. 10, it is determined that the local structure LS1 in the proximity of the candidate point in the target region E1 is the spherical marker BM. Whereas, referring to FIG. 10, it is determined that the local structure LS2 in the proximity of the candidate point in the target region E2 is not the spherical marker BM, so that such local structure is removed in the following processings.

The device location acquisition element 66 acquires the gravity center of the local structure as the location of the local structure that the device determination element 64 determines as the spherical marker BM. The gravity center coordinate of the spherical marker BM that is a sphere is given by the following formula (1).

Mathematical Formula (I)

$$x_G = \frac{m_1 x_1 + m_2 x_2 + \ldots + m_n x_n}{m_1 + m_2 + \ldots + m_n} \quad (1)$$

wherein, $x_g$ $x_G$ is a location vector of the gravity center, $x_n$ is a pixel location vector of the local structure and inn is an inversed pixel value. In such way, according to the formula (1), the inversed pixel value is used, and given the smaller the pixel value is, the larger the mass is, the coordinate of the gravity center that is the center of the spherical marker BM is calculated. Accordingly, the gravity center coordinate of the spherical marker BM at each frame can be in the unit of sub-pixel (e.g., 1/10 pixel).

The device tracking element 67 tracks the marker based on the location of the marker in each frame that the device location acquisition element 66 acquires. Referring to FIG. 11, the image 95 is the image in which the continuous three frames, of which the location of the spherical marker. BM is already acquired, are superimposed. Referring to FIG. 11, relative to the location n of the spherical marker BM of the frame to calculate the location of the device, the location n of the spherical marker BM can be predicted by calculating the moving rate and the acceleration of the spherical marker BM from the location n-1, n-2, n-3, of the spherical marker of the previous few frames. In such way, the device tracking element 67 predicts the location n of the spherical marker BM in the next frame, and specifies the vicinity of the location of the spherical marker BM for the device searching target region SE in the next frame. Therefore, the deviation of the device searching is prevented, so that the acquisition and tracking of the location of the marker in each frame can be promptly carried out and the suspension of the marker tracking can be prevented.

The calculation for the spatial location of the spherical marker to irradiate accurately the affected area that moves due to breathing and so forth is repeatedly executed by utilizing the recognition and tracking result of the spherical marker by each functional structure as set forth above. The 3-dimension absolute coordinate acquisition element 68 acquires the 3-dimension absolute coordinate from the location of each marker and the marker tracking result in the 2-dimension image that is obtained from two directions using the device location acquisition element 66 and the device tracking element 67, by applying the relationship of the epipolar geometry.

Since then the gating signal output element 69 sends the gating signal to the radiation therapy apparatus to irradiate the therapeutic beam to the subject 57 when the 3-dimension absolute coordinate that the 3-dimension absolute coordinate acquisition element 68 acquires is in the predetermined range. Specifically, the gating signal output element 69 generates the signal to control ON-and-OFF of the therapeutic beam to irradiate the therapeutic beam to the moving affected region only when the affected region is located within the specific region out of the location of the marker.

According to the aspect of the present Embodiment as set forth above, the template matching to recognize the marker is not carried out, so that the preparation time for ftuoroscoping the subject 57 to generate the template for the template matching in advance can be cut. Accordingly, the throughput of the radiation therapy apparatus can be improved.

In addition, according to the conventional template matching, the contrast of the marker is different between the images depending on overlapping with the structure such as bone and so forth inside the body and the locational relationship, so that a plurality of templates having a different contrast are prepared and the matching operation relative to the template must be repeated until the degree of matching higher than the predetermined threshold value is calculated. According to the aspect of the present Embodiment, the matching operation is not carried out, so that the time needed for marker recognition can be cut. Further, the device candidate detection element 62 removes the structure such as bone and so forth inside the body from the image, so that the contrast difference is much less effective, and the detection of the marker can be executed more effectively.

Figure 12:
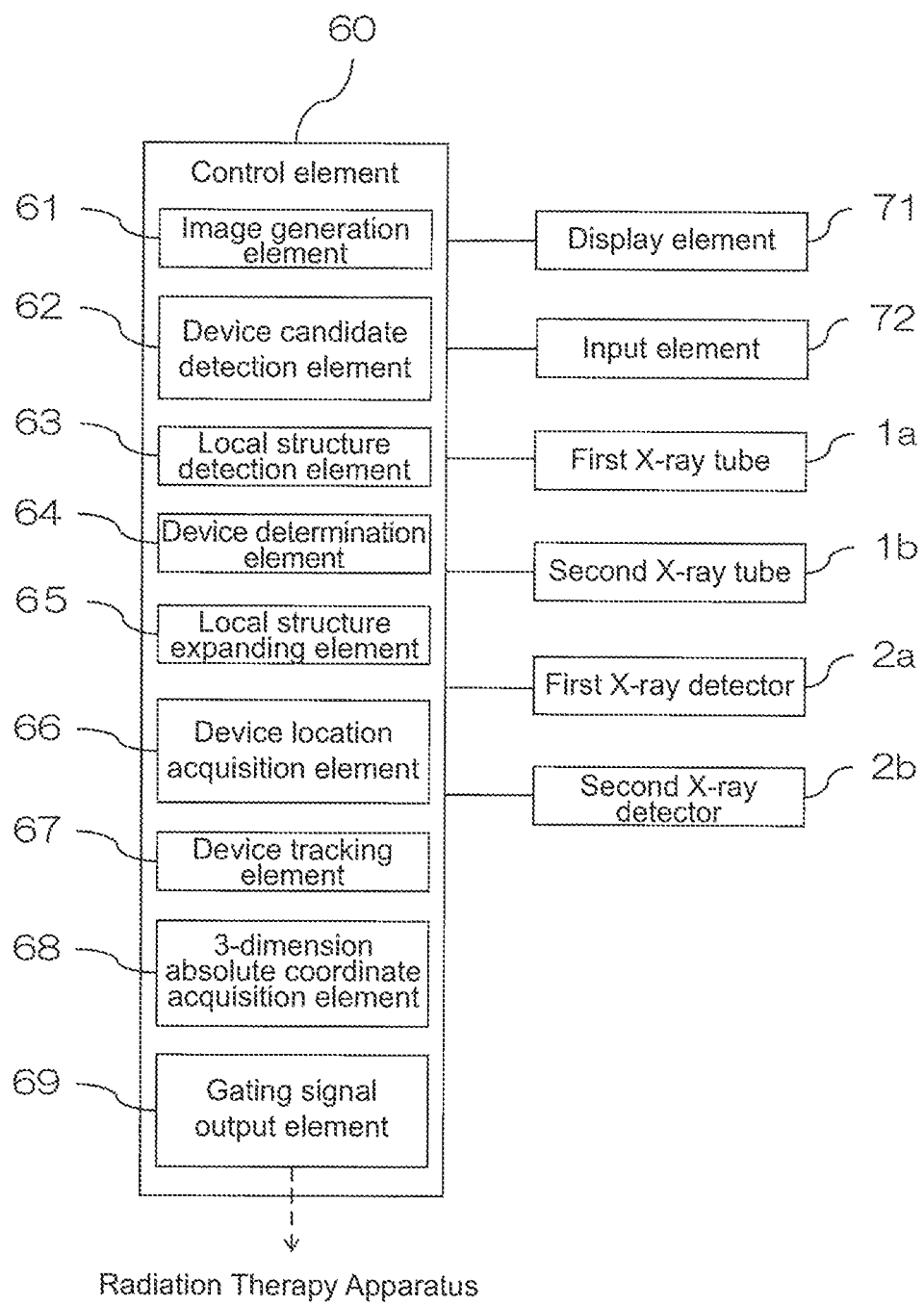
FIG. 12 is a block diagram illustrating the main control system of the X-ray fluoroscopy apparatus according to an aspect of the Embodiment 2 of the present invention.

Next, the inventor sets forth the other Embodiment of the present invention. FIG. 12 is a block diagram illustrating the main control system of the X-ray fluoroscopy apparatus according to an aspect of the Embodiment 2 of the present invention. The control element 60 according to the aspect of the present Embodiment further comprised a local structure expanding element 65. Further, the same functional structure as illustrated according to the aspect of the Embodiment 1 set forth above is not set forth in detail.

Figure 13:
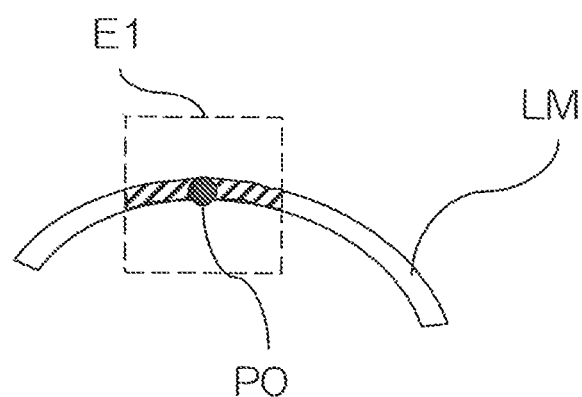
FIG. 13 is a schematic view illustrating the operation of the local structure detection element 63.
Figure 14A:
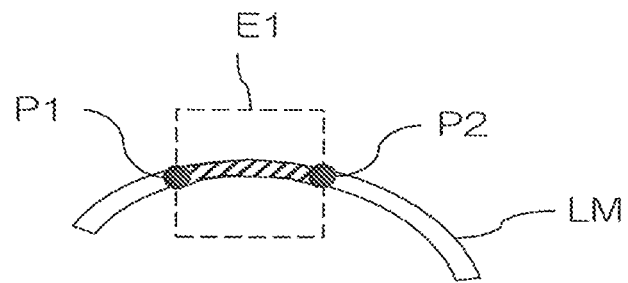
FIG. 14A, 14B, 14C are schematic views illustrating the operation of the local structure expanding element 65.
Figure 14B:
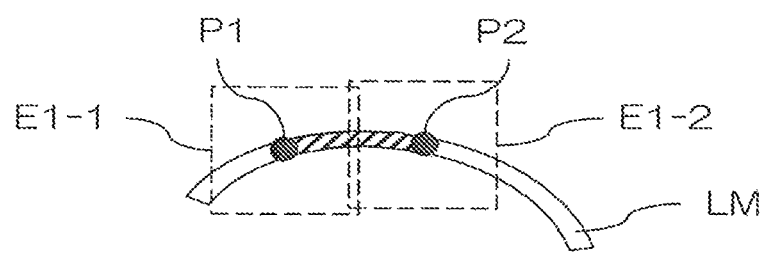
Figure 14C:
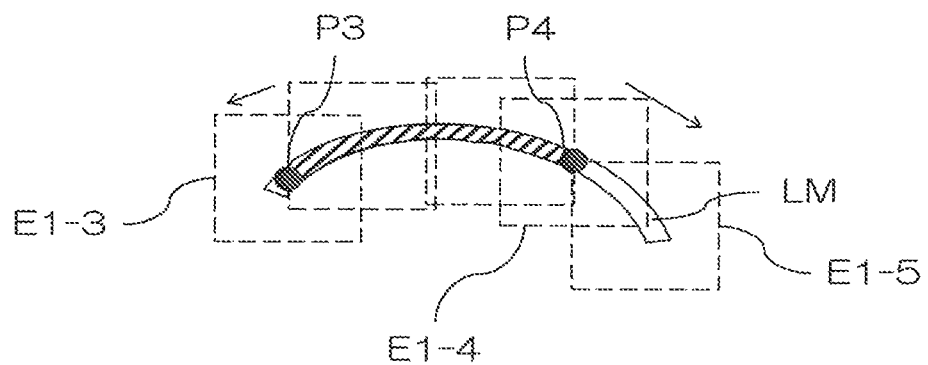
Figure 15:
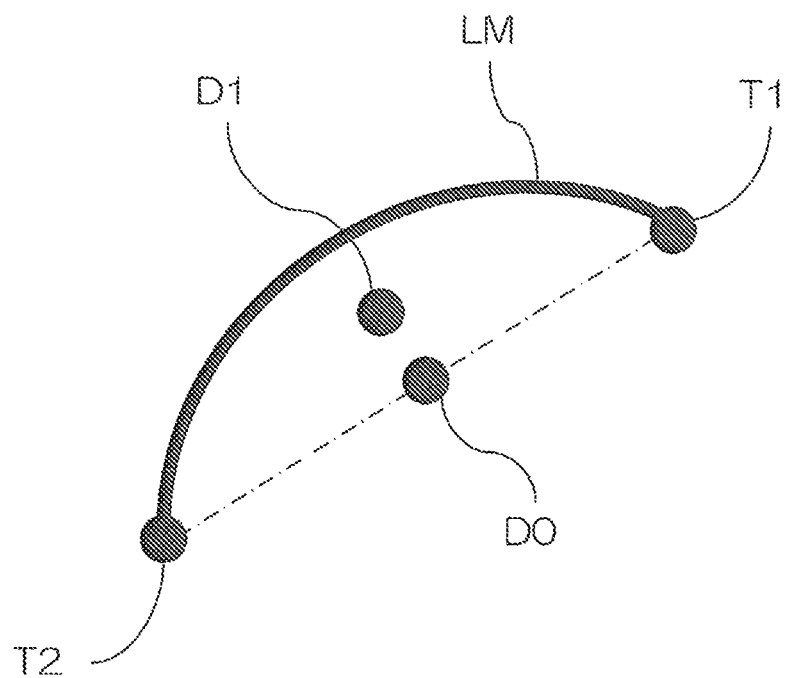
FIG. 15 is a schematic view illustrating the operation of the device location acquisition element 66.

Next, the inventor sets forth an example of the case in which the marker embedded inside the body of the subject 57 is a non-spherical curved marker. FIG. 13 is a schematic view illustrating the operation of the device candidate detection element 62 and the local structure detection element 63. FIG. 14A, 14B, 14C are schematic views illustrating the operation of the local structure expanding element 65. FIG. 15 is a schematic view illustrating the operation of the device location acquisition element 66.

First, the device candidate detection element 62 detects the candidate point of the curved marker LM from the image that the image generation element 61 generates. Referring to FIG. 13, as well as the Embodiment 1, the image 92 from which the static structure such as bone and so forth is removed is generated and the candidate point P0 is detected.

The local structure detection element 63 executes the local segmentation in a proximity of the candidate point P0 of the curved marker LM that the device candidate detection element 62 detects in the predetermined target regions E1, and detects the local structure (indicted with hatching in FIG. 13). Such local structure is detected using the same method applied in the Embodiment 1 with regard to the predetermined target region E1 having the candidate point P0 at the center thereof.

The device determination element 64 determines whether the local structure that the local structure detection element 63 detects is the curved marker LM or not. The non-spherical curved marker LM appears with a variety of directions and lengths in the image depending on the fluoroscopy direction differently from the spherical marker BM set forth relative to the Embodiment 1. In addition, the shape thereof per se varies along with the movement inside the body. Whereas the shape thereof, when viewing locally the curved marker LM while further segmenting into the narrow region, can be deemed as a cluster of lines, and also a cluster of fine lines having a different gradient. In addition, the line thickness of the curved marker LM appearing in the image can be easily estimated based on the size of the curved marker LM. Therefore, the device determination element 64 determines that the local structure that have the line shape and of which the area is in the predetermined range is a part of the curved marker LM. A response to the known eight directions Gabor filters capable of extracting which line is included is applied to determination of the shape.

The local structure expanding element 65 detects one overall structure, i.e., an entire structure of the curved marker LM, from the local structure that is a part of the curved marker LM. Given the local structure that the local structure detection element 63 detects is the part of the curved marker LM, it is implied that the end of the predetermined target region E1 that the local structure detection element 63 specifies is overlapped with the local structure. The expansion relative to such local structure expanding element 65 is executed by that; referring to FIG. 14A, the end of the local structure located at the end of the predetermined target region E1 having the candidate point P0 as the center thereof is specified as the new candidate points P1, P2 of the curved marker LK and further, referring to FIG. 14B, the predetermined target regions E1-1, E1-2 having each candidate point P1. P2 as the center thereof are specified; and the local structure detection element 63 detects the local structures at the new predetermined target regions E1-1, E1-2 (i.e., segmentation processing). Specifically, each operation of the specification of the new candidate point and target regions and the segmentation processing is repeated so that the local structure is expanded the overall structure corresponding to the entire image of the curved marker LM. In such way, whether the curved marker LM is or not is determined following the resolution of the curved marker LM into the local structures in some regions, so that an effect due to deformation and rotation can be limited. In addition, such expansion operation is continued until the local structure that reaches to the end of the predetermined target region is gone.

Referring to FIG. 14C, the direction in which the local structure is expanded to the overall structure and the direction in which the new candidate points P3, P4 and the predetermined target regions E1-3, E1-4 having the candidate points P3, P4 as the center thereof are specified are designated to be the constant direction. Such designation can be achieved utilizing the direction of the line of the local structure that is acquired by application of the eight directions Gabor filter. In such way, once the extending direction of the local structure is defined, even when the curved marker LM is overlapped with a noise, the local structure is never expanded in the direction, in which the noise expands, that is the different direction from the direction of the local structure that is determined as a part of the curved marker LM. Therefore, the curved marker LM having the different facing direction, length, and shape in the image depending on the fluoroscopy direction and the embedded place can be accurately detected.

In addition, in the case of the curved marker LM, the device candidate detection element 62 may detect a plurality of candidate points relative one curved marker LM in the image. However, even when the detection and the expansion of the local structure from each candidate point are carried out, the overall structure having the shape of one curved marker LM is collectively obtained as the bottom line, so that an overlapping of the candidate points on the one curved marker LM never effects on the recognition of the curved marker LM. Therefore, according to the aspect of the present Embodiment, the marker can be recognized with a high degree of accuracy regardless the shape of the marker.

The device location acquisition element 66 acquires a gravity center D0, end points T1, T2 and a center point D1 of the overall structure obtained by the operation of the local structure expanding element as the location of the curved marker LM (referring to FIG. 1). The coordinate of the gravity center D0 of the curved marker LM is calculated using the formula (1) as well as the aspect of the Embodiment 1. Referring to FIG. 14, the end points T1, T2 are also the end of the expanded local structure, so that the coordinate of the end points T1, T2 is calculated utilizing the direction of the local structure at the end that the multi directions Gabor filter provides. And the center point D1 is the center point between both ends of the end points T1, T2 and calculated using the coordinate of the end points T1, T2.

In such way, according to the aspect of the present Embodiment, the device location acquisition element 66 acquires the plurality of coordinates as the location of the device so that the device can be tracked using the most adequate location for tracking the curved marker LM depending on the level of the locational relationship between the curved marker LM and the affected region inside the body of the subject 57 and the deformation and rotation thereof, so that the suspension of the tracking of the curved marker LM can be prevented.

As well as the aspect of the Embodiment 1, once the location of the curved marker LM in each frame is acquired, the device determination element 67 executes tracking the curved marker LM, and farther, the 3-dimension absolute coordinate acquisition element 68 acquires the 3-dimension absolute coordinate of the curved marker LM. Since then the gating signal output element 69 generates the gating signals and sends such signals to the radiation therapy apparatus to irradiate the therapeutic beam to the subject 57 when the 3-dimension absolute coordinate of the curved marker LM is in the predetermined range.

In addition, the device according to the aspect of the present invention is not limited to the spherical marker BM and the curved marker LM as set forth according to the aspect of the Embodiments, and for example, includes a guide wire and a stent that are inserted into coronary artery in the CAG (coronary angiogram) using the X-ray fluoroscopy apparatus. In addition, in the CAG, the guide wire and the stent move severely due to heartbeat, so that an aspect to execute an affine transformation (translation, rotation and deformation) of the image in each frame that the image generation element 61 generates can be added to display the device such as the guide wire and the stent and so forth on the display element 71 as if fixed in the image. In addition, when the aspect by which carries out the integration in the time direction using the known recursive filter and so forth relative to the image in each frame following the affine transformation is further added, the device image having no movement and less noises can be obtained.

REFERENCE OF SIGNS

1a First X-ray tube
1b Second X-ray tube
2a First X-ray detector
2b Second X-ray detector
3a X-ray tube first pedestal
3b X-ray tube second pedestal
4a First pedestal for X-ray detector
4b Second pedestal for X-ray detector
10 Move passage
11 First rail
12 Second rail 20 Move passage
21 First rail
22 Second rail
51 Floor surface
53 Gantry
54 Head support element
55 Head
56 Table
57 Subject
60 Control element
61 Image generation element
62 Device candidate detection element
63 Local structure detection element
64 Device determination element
65 Local structure expanding element
66 Device location acquisition element
67 Device tracking element
68 3-dimension absolute coordinate acquisition element
69 Gating signal output element
71 Display element
72 Input element
91 Image
92 image
93 Image
95 Image Although only a few embodiments have been disclosed in detail above, other embodiments are possible and the inventors intend these to be encompassed within this specification. The specification describes certain technological solutions to solve the technical problems that are described expressly and inherently in this application. This disclosure describes embodiments, and the claims are intended to cover any modification or alternative or generalization of these embodiments which might be predictable to a person having ordinary skill in the art.

Also, the inventors intend that only those claims which use the words "means for" are intended to be interpreted under 35 USC 112, sixth paragraph. Moreover, no limitations from the specification are intended to be read into any claims, unless those limitations are expressly included in the claims.

Having described at least one of the preferred embodiments of the present invention with reference to the accompanying drawings, it will be apparent to those skills that the invention is not limited to those precise embodiments, and that various modifications and variations can be made in the presently disclosed system without departing from the scope or spirit of the invention. Thus, it is intended that the present disclosure cover modifications and variations of this disclosure provided they come within the scope of the appended claims and their equivalents.

What is claimed is:

1. A radiation fluoroscopy apparatus, comprising:
   a radiation source; and
   a radiation detector that detects a radiation that is irradiated from said radiation source and transmits a subject;
   wherein said radiation fluoroscopy apparatus detects a location of a device in an image, including an embedded device inside a body of said subject, which is obtained by a fluoroscopy that is carried out from a plurality of directions at a predetermined frame rate, and tracks a movement of said device, and further comprising;
   an image generation element that generates said image including said device based on a detection signal of said radiation detector;
   a local structure detection element that detects a local structure in said image, including said device, which said image generation element generates;
   a device determination element that determines whether said local structure that said local structure detection element detects is said device or not;
   a device location acquisition element that acquires said location of said local structure in said image as a location of said device that said device determination element determines as said device; and
   a device tracking element that tracks said device based on said location of said device in each frame that said device location acquisition element acquires.

2. The radiation fluoroscopy apparatus, according to claim 1, further comprising:
   a device candidate detection element that detects a candidate of said device in said image including said device;
   wherein said local structure detection element detects said local structure in a proximity of said candidate of said device that said device candidate detection element detects.

3. The radiation fluoroscopy apparatus, according to claim 2, further comprising:
   a local structure expanding element that detects one overall structure corresponding to a whole of said device based on said local structure when said device determination element determines that said local structure that said device determination element determines to be said device is a part of said device.

4. The radiation fluoroscopy apparatus, according to claim 2, wherein:
   said device location acquisition element acquires a gravity center of said local structure, which said device determination element determines to be said device, as a location of said device.

5. The radiation fluoroscopy apparatus, according to claim 1, further comprising:
   a local structure expanding element that detects one overall structure corresponding to a whole of said device based on said local structure when said device determination element determines that said local structure that said device determination element determines to be said device is a part of said device.

6. The radiation fluoroscopy apparatus, according to claim 5, wherein:
   said device location acquisition element acquires a gravity center, an end point and a center point of said overall structure, which said local structure expanding element acquires, as the location of said device.

7. The radiation fluoroscopy apparatus, according to claim 1, wherein:
   said device location acquisition element acquires a gravity center of said local structure, which said device determination element determines to be said device, as a location of said device.

* * * * *